United States Patent [19]
Heath et al.

[11] Patent Number: 5,766,617
[45] Date of Patent: Jun. 16, 1998

[54] TRAPPING SYSTEM FOR MEDITERRANEAN FRUIT FLIES

[75] Inventors: Robert R. Heath; Nancy D. Epsky, both of Gainesville, Fla.

[73] Assignee: The United States of America as represented by the Secretary of Agriculture, Washington, D.C.

[21] Appl. No.: 702,371

[22] Filed: Aug. 23, 1996

[51] Int. Cl.$^6$ .......................... A01N 25/10; A01N 33/02
[52] U.S. Cl. ................ 424/410; 424/407; 424/77; 514/554; 514/663
[58] Field of Search .................... 424/84, 407, 410; 514/554, 66 B

[56] References Cited

U.S. PATENT DOCUMENTS

| | | | |
|---|---|---|---|
| 3,996,349 | 12/1976 | Mulla et al. | 424/84 |
| 4,122,165 | 10/1978 | Kinzer et al. | 424/84 |
| 5,399,344 | 3/1995 | Yang | 424/84 |

OTHER PUBLICATIONS

Qureshi et al., *Pakistan J. Sci. Ind. Res.*, vol. 19(1), pp. 22–23 (1976).
Bailey et al., *J. Econ. Entom.*, vol. 63(6), pp. 2000–2001 (1970).
Heugens, A., *Med. Fac. Landbouww*, Univ. Gent, 59/2b, pp. 587–597 (1994).
Robacker et al., *J. Chem. Ecol.*, vol. 19(12), pp. 2999–3016 (1993).
Winder, G., *Pl. Path.*, vol. 20, pp. 164–166 (1971).
Chapman et al., *Pestic. Sci.*, vol. 36, pp. 35–45 (1992).
Robacker et al., *Annals Entom. Soc. Amer.*, vol. 84(5), pp. 555–559 (1991).
Robacker et al., *J. Chem. Ecol.*, vol. 19(3), pp. 543–557 (1993).
Robacker et al., *J. Chem. Ecol.*, vol. 22(2), pp. 499–511 (1996).
Heath et al., *Florida Entomologist*, vol. 79(2), pp. 144–153 (1996).
Heath et al., *Florida Entomologist*, vol. 79(1), pp. 37–48 (1996).
Enkerlin et al., Chapter 2.7, "Mexico, Central and South America", pp. 83–90 in S. Robinson and G. Hooper [eds.], World Crop Pests, vol. 3A, Fruit flies, their biology, natural enemies and control. Elsevier Science Publishers B.V. Amsterdam (1989).
Epsky et al., Environ. Entomol. 24(6): 1387–1395 (1995).
Gilbert et al., Insect Trapping Guide, Second Edition, pp. MF–1–MF–7 and MEX–1–MEX–4 (Jul. 1984).
Harris et al., J. Econ. Entom. 61(1): 62–65 (1971).
Heath et al., Florida Entom. 79(2): 144–153 (1996).
Heath et al., Florida Entom. 79(1): 37–48 (1996).
Heath et al., J. Econ. Entom. 88(5): 1307–1315 (1995).
Lance et al., J. Econ. Entomol. 87(6): 1377–1383 (1994).
McPhail, M., J. Econ. Entomol. 32(6): 758–761 (1939).
Nakagawa et al., J. Econ. Entomol. 63(1): 227–229 (1970).
Newell, W., J. Econ. Entomol. 29(1): 116–121 (1936).
Robacker et al., J. Chem. Ecology 12(1): 39–47 (1986).
Robacker, D., Environ. Entomol. 20(6): 1680–1686 (1991).
Robacker, D., Florida Entomologist 75(2): 230–241 (1992).
Robacker, D., Florida Entomologist 78(4): 571–578 (1995).
Robacker et al., J. Chem. Ecol. 21(11): 1861–1873 (1995).
Robacker et al., J. Chem. Ecol. 16(6): 2027–2037 (1990).
Robacker et al., Environ. Entomol. 22(6): 1367–13 (1993).
Robacker et al., Florida Entomologist 78(1): 62–69 (1995).
Robacker et al., J. Chem. Ecol. 19(12): 2999–3016 (1993).
Robacker et al., Environ. Entomol. 19(2): 403–408 (1990).
Robacker et al., J. Chem. Ecol. 16(10): 2799–2815 (1990).

(List continued on next page.)

*Primary Examiner*—Neil S. Levy
*Attorney, Agent, or Firm*—M. Howard Silverstein; John Fado; Gail E. Poulos

[57] ABSTRACT

A trapping system for capturing male and female frugivorous pest insects for detecting, monitoring, and/or controlling that includes an attractant composition of ammonium acetate and putrescine and a synergist for the attractant composition.

4 Claims, 6 Drawing Sheets

OTHER PUBLICATIONS

Robacker et al., J. Chem. Ecol. 19(3): 543–557 (1993).
Robacker et al., J. Chem. Ecol. 22(3): 499–511 (1996).
Steiner, L. J. Econ. Entomol. 58(2): 374–375 (1965).
Anonymous, Florida Fruit Fly Detection Manual, USDA, APHIS, PPQ & FLDACS, DPI, Gainesville, FL 1989.
Baker et al., Journal of Economic Entomology 83: 2235–2245, 1990.
Bateman & Morton, Aust. J. Agric. Res. 32:883–903, 1981.
Beroza et al., J. Agric. Food Chem. 9: 361–365, 1960.
Box et al., Statistics for Experimenters: An Introduction to Design, Data Analysis, and Model Building, J. Wiley & Sons, NY, 1978.
Buttery et al., J. Agric. Food Chem. 31:689–692, 1983.
Chrisentson & Foote, Annual Review of Entomology 5:171–192, 1960.
Greany et al., Entomol. Exp. Appl. 21: 63–70, 1977.
Heath et al., Journal of Chemical Ecology 17: 1925–1940.
Jones et al., Bulletin of Entomological Research 73:97–106, 1983.
Keiser et al., Journal of Economic Entomology 69: 517–520, 1976. Replaces Keiser et al., Lloydia 38: 141–152, 1976.
Kydonieus, Agis F., Controlled Release Pesticides, Scher [ed.], ACS Symposium Series 53, American Chemical Society, Washington, DC. 152–167. 1977.
Landolt et al., Environmental Entomology 21: 1154–1159, 1992.
Leonhardt et al., Insect Pheromone Technology: Chemistry and Applications, ACS Symposium Series 190, American Chemical Society, Washington, DC. 159–173, 1982.
Mazomenos & Haniotakis, Journal of Chemical Ecology 11:397–405, 1985.
Mazor et al., Entomol. Exp. Appl. 43: 25–29, 1987.
McPhail, Journal of Economic Entomology 32: 758–761, 1939.
Morton & Bateman, Aust. J. Agric. Res. 32: 905–916, 1981.
Nakagawa et al., Journal of Economic Entomology 63: 227–229, 1970.
Nakagawa et al., Entomol. Exp. Appl. 24: 193–198, 1978.
Prokopy, Environmental Entomology 1: 720–726, 1972.
Prokopy, Canadian Entomologist 109: 593–596, 1977.
Prokopy & Boller Journal of Economic Entomology 64: 1444–1447, 1971.
Prokopy & Economopoulos, Z Ang. Entomol. 80: 434–437, 1976.
Riedl & Hislop, Environmental Entomology 14: 810–814, 1985.
Reissig et al., Environmental Entomology 11: 1294–1298, 1982.
SAS Institute, SAS/STAT Guide for Personal Computers, ver. 6 ed., SAS Institute, Cary, NC, 1985.
Steyskal, Florida Entomologist 60: 11–16, 1977.

Fig. 4a  FEMALES

Fig. 4b  MALES

Fig. 4c  TOTAL

TRAPPING SYSTEM FOR MEDITERRANEAN FRUIT FLIES

BACKGROUND OF THE INVENTION

1. Field of the Invention

The present invention relates to a novel composition, trapping system and method for monitoring and/or controlling Mediterranean fruit flies.

2. Description of the Related Art

Control of frugivorous pest flies, such as the Mediterranean fruit fly, *Ceratitis capitata* (Weidemann) and the Mexican fruit fly, *Anastrepha ludens* (Loew), is of considerable economic importance for fruit and vegetable production and export. Quarantine and regulatory agents expend substantial efforts to detect newly introduced species of economically important fruit flies. The Mediterranean fruit fly, *Ceratitis capitata* is a major frugivorous pest due to its wide distribution and large host range (Enkerlin et al., World Crop Pests, Vol. 3A; Fruit Flies, Their Biology, Natural Enemies and Control, Elsevier Science Publishers, 1989). Because of the threat of the potential introduction of the Mediterranean and Mexican fruit flies into areas of the world currently free from these pests, such as for example the United States, much emphasis has been placed on detection and eradication of these species. The development of improved lures is needed to monitor and suppress populations of this and other pest fruit flies, and to prevent establishment of populations in areas that are currently without these pests.

Methods developed for monitoring, controlling, and eradicating frugivorous fruit flies (Tephritidae) have relied extensively on the use of chemical attractants. Methyl eugenol plus dibrom; cuelure plus dibrom; ammonium salts; and a mixture of 1,7-dioxaspiro [5.5] undecane with α-pinene or n-nonanal; and spiroacetal are used as lures for species of Dacus. A composition of hexyl acetate, (E)-2-hexen-1yl acetate, butyl 2-methylbutanoate, propyl hexanoate, hexyl propanoate, butyl hexanoate, and hexyl butanoate is used as a lure for species of Rhagoletis. Effective insect-detection systems are essential for preventing the establishment of pests such as these fruit flies and surveys for these flies are included in state and federal exotic pest-detection programs in at least nine southern and southwestern states (Lance and Gates, *J. Econ. Entomol.*, Volume 87, 1377–1383, 1994). California, Texas and Florida maintain large number of trimedlure-baited Jackson traps (Harris et al, *J. Econ. Entomol.*, Volume 64, 62–65, 1971) for the detection of male *C. capitata* and aqueous protein-baited McPhail traps (Newell, *J. Econ. Entomol.*, Volume 29, 116–120, 1936; McPhail, *J. Econ. Entomol.*, Volume 32, 758–761, 1939) for detection of male and female *C. capitata* and *A. ludens* (USDA, National exotic fruit fly trapping protocol. Animal and Plant Health Inspection Service, Plant Protection and Quarantine, Hyattsville, Md., 1991). McPhail traps are currently used for monitoring fruit flies throughout fruit growing areas of the world. There are several problems associated with use of either of these trapping systems. Although trimedlure is effective in attracting male Mediterranean fruit flies, it is either only weakly active in attracting or is completely ineffective in attracting female Mediterranean fruit flies (Nakagawa et al., *Journal of Economic Entomology* 63: 227–229, 1970). Inability to capture female *C. capitata* limits the effectiveness of trimedlure-baited traps as a control device and no information on population dynamics of the female flies is obtained. McPhail traps, bell-shaped glass traps with a water reservoir containing aqueous protein baits, offer the advantage of attracting both male and female *C. capitata* and *A. ludens* fruit flies, however, these traps are cumbersome and have numerous disadvantages of their own. Servicing the trap requires that water and bait be added in a somewhat maladroit manner in which the trap is turned upside down, bait added and then the trap returned to an upright position. This process often results in bait spillage, and the spilled bait becomes a food source for flies outside the trap. Removal of insects trapped requires considerable effort. The contents of the trap must be filtered through a screen to separate the insects from the bait solution. Trapped fruit flies are often found severely decomposed with parts missing and thus, when these traps are used in conjunction with marked flies in sterile release programs (Steiner, J. Econ. Entomol., Volume 58, 374–375, 1965), difficulty is encountered in determining whether a trapped fly is a sterile or a wild fly. Other factors that contribute to the difficulty in the deployment of McPhail traps include the size and weight of the trap, and the fragile nature of glass. Protein baits also attract a number of non-targeted insects and considerable time is required to sort among the trapped insects.

Conventional lures currently used to survey and detect frugivorous pests are protein baits such as fermenting yeast hydrolysate (Greany et al., *Ent. exp & Appl.* 21:63–70, 1977) and protein hydrosylate (McPhail, *J. Econ. Entomol.* 32:758–761, 1939). The problem with protein lures is that they capture large numbers of nontarget insects. Furthermore, the only lures that are available for attracting both female and male fruit flies are protein baits.

Adult fruit flies require sugar to survive (Christenson & Foote, *Annual Review of Entomology* 5:171–192, 1960), and honeydew secreted by homopterous insects is recognized as an important food source for adult tephritids (Christenson et al., *Annual Review of Entomology* 5:171–192, 1960). Female fruit flies also require protein to ensure fecundity, and this protein requirement is the primary basis for traps for detection of female fruit flies. McPhail traps are cumbersome and use of these traps have numerous disadvantages.

Hundreds of compounds are known to be released from protein baits (Morton & Bateman, *Aust. J. Agric. Res.* 32:905–916, 1981). Examples of some volatile components of commercial hydrolyzed protein insect baits are phenylacetaldehyde, acetic acid, furfuryl alcohol, 2-acetylfuran, benzaldehyde, methanol, 2-acetylpyirole, furfural, 5-methyl-2-phenyl-2-hexenal, 5-methyl-2| (methylthio)methyl|-2-hexenal and ammonia. Ammonia (Bateman & Morton, Aust. J. Agric. Res. 32:883–903, 1981; Mazor et al., *Entomol. Exp. Appl.* 43:25–29, 1987), acetic acid (Keiser et al., *Lloydia* 38: 141–152, 1976), and various other volatiles (Buttery et al., *J. Agric. Food Chem.* 31: 689–692, 1983) have been investigated as attractants for fruit flies. Robacker et al (*Fla. Entomol.*, Volume 78, 571–598, 1995; Robacker, *J. Chem. Ecology*, Volume 19, 2999–3016, 1993) report that methylamine, a monosubstituted ammonia, is an attractant for *A. ludens*. These reports, however, do not provide information regarding released amounts or ratios of the compounds tested or the effectiveness of these chemicals as compared to McPhail traps.

Due to the difficulties associated with McPhail traps, investigations to develop a dry insect trap with food-based attractant for monitoring *C. capitata* fruit flies were undertaken which resulted in U.S. patent application Ser. Nos. 08/647,211 filed May 09, 1996, which is a file wrapper continuation of patent application Ser. No. 08/231,213, filed Apr. 22, 1994, now abandoned; and 08/440,023, a divisional of 08/231,213, filed May 12, 1995, all herein incorporated by reference. All disclose a novel trapping system to enable the use of dry traps and include a synthetic food-based chemical attractant that is ammonium acetate and putrescine.

While there are various methods and compositions for monitoring and/or controlling frugivorous pests, especially the Mediterranean fruit fly, there remains a need in the art for an effective system that captures both male and female flies. The present invention provides a system and a method which is different from the prior art and overcomes problems associated with capture systems and methods of monitoring and/or controlling frugivorous pests, especially the Mediterranean fruit fly.

SUMMARY OF THE INVENTION

It is, therefore, an object of the present invention to provide a system for monitoring and/or controlling frugivorous pest insects using food-based chemical stimuli that includes a tri-substituted ammonia in synergistic amounts.

Another object of the present invention is to provide a combination of a trap and chemical stimuli that attracts frugivorous pest insects and induces them to be trapped.

Still another object of the present invention is to provide a trap for frugivorous pest insects that contains a food-based chemical bait made up of ammonium acetate, putrescine, in effective amounts to attract frugivorous pests; and trimethyl amine in synergistic amounts.

A further object of the present invention is to provide a composition for attracting frugivorous pest insects that includes ammonium acetate,1,4-diaminobutane and trimethyl amine.

Further objects and advantages of the invention will become apparent from the following description.

BRIEF DESCRIPTION OF THE DRAWINGS

FIG. 4a is a graph showing percentage of *Anastrepha ludens* females captured in opaque open bottom cylinderical traps baited with ammonium acetate and putrescine (PT-AA+P), opaque open bottom cylinderical traps baited with ammonium acetate, putrescine and trimethyl amine (PT-AA+P+TMA), sticky cylinderical traps baited with ammonium acetate, putrescine and trimethylamine (FFAP+AA+P+TMA), McPhail traps with torula yeast (Mc+Ty), McPhail traps baited with ammonium acetate, and putrescine(Mc+AA+P), McPhail traps baited with ammonium acetate, putrescine and trimethyl amine (Mc+AA+P+TMA) and McPhail traps baited with ammonium acetate, putrescine and dimethyl amine (Mc+AA+P+DMA). Bars headed by the same letter within a graph are not significantly different (LSD mean separation on square root [x=0.5] transformed data, P=0.05; non-transformed means presented).

FIG. 4b is a graph showing percentage of *Anastrepha ludens* males captured in opaque open bottom cylinderical traps baited with ammonium acetate and putrescine (PT-AA+P), opaque open bottom cylinderical traps baited with ammonium acetate, putrescine and trimethyl amine (PT-AA+P+TMA), sticky cylinderical traps baited with ammonium acetate, putrescine and trimethylamine (FFAP+AA+P+TMA), McPhail traps with torula yeast (Mc+Ty), McPhail traps baited with ammonium acetate, and putrescine(Mc+AA+P), McPhail traps baited with ammonium acetate, putrescine and trimethyl amine (Mc+AA+P+TMA) and McPhail traps baited with ammonium acetate, putrescine and dimethyl amine (Mc+AA+P+DMA). Bars headed by the same letter within a graph are not significantly different (LSD mean separation on square root [x=0.5] transformed data, P=0.05; non-transformed means presented).

FIG. 4c is a graph showing percentage of *Anastrepha ludens* females plus males captured in opaque open bottom cylinderical traps baited with ammonium acetate and putrescine (PT-AA+P), opaque open bottom cylinderical traps baited with ammonium acetate, putrescine and trimethyl amine (PT-AA+P+TMA), sticky cylinderical traps baited with ammonium acetate, putrescine and trimethylamine (FFAP+AA+P+TMA), McPhail traps with torula yeast (Mc+Ty), McPhail traps baited with ammonium acetate, and putrescine(Mc+AA+P), McPhail traps baited with ammonium acetate, putrescine and trimethyl amine (Mc+AA+P+TMA) and McPhail traps baited with ammonium acetate, putrescine and dimethyl amine (Mc+AA+P+DMA). Bars headed by the same letter within a graph are not significantly different (LSD mean separation on square root [x=0.5] transformed data, P=0.05; non-transformed means presented).

DETAILED DESCRIPTION THE INVENTION

The invention provides a system for monitoring and/or controlling Mediterranean fruit flies without using aqueous protein solutions. The method and apparatus of the invention incorporate a unique combination of a trapping means and chemical stimuli which attracts, traps and/or kills frugivorous pests.

A trapping means is any device for catching pest insects, especially frugivorous pest insects that includes for example, cylindrical traps, especially sticky paper cylindrical traps; and McPhail traps. Sticky paper cylindrical traps are most preferred.

Chemical stimuli includes ammonia, acetic acid and putrescine(1,4-diaminobutane). Ammonium acetate can be substituted for the ammonia and acetic acid. An effective amount of each of these compounds is defined as that quantity of chemical blend that provides a release rate of the blend that attracts fruit flies to the location containing the stimuli at a rate significantly higher than flies are attracted to a location where the stimuli is absent.

A synergist for the chemical stimuli is defined as any tri-substituted ammonia that significantly increased the attractiveness of the chemical stimuli as defined above. Trialkyl-substituted ammonia is preferred and trimethyl amine is most preferred. A synergistic amount, effective amount, or synergistically effective amount is defined as that quantity of tri-substituted ammonia that significantly increases the attraction of fruit flies to a location that contains the above defined chemical stimuli at a rate significantly higher than the rate flies are attracted to a location containing the stimuli alone.

It has been discovered that the addition of a tri-substituted ammonia, especially trimethyl amine, to the prior art lure of ammonium acetate and putrescine affords a significant synergistic affect on the capture of *C. capitata*. Field trials were conducted in Guatemala to determine the synergistic effect of methyl amine, dimethyl amine and trimethyl amine when added to a synthetic food based attractant used for detection of *Ceratitis capitata* (Wiedemann) and *Anastrepha ludens* (Loew). Captures of wild male and female *C. capitata* were improved when trimethyl amine is added to a synthetic blend of ammonium acetate and putrescine. The addition of methyl amine or dimethyl amine to traps containing ammonium acetate and putrescine verses ammonium acetate and putrescine baited traps resulted in similar trap capture. Traps baited with the different combination of synthetic lures captured more *C. capitata* then McPhail traps baited with torula yeast. Capture of male and female *A. ludens* in traps baited with synthetic lures was not affected by the addition of any of the amines. Capture of female *A. ludens* was lower in traps baited with ammonium acetate, putrescine and trimethyl amine compared to torula yeast baited McPhail traps. A comparison of trap capture in open bottom cylinderical traps containing synthetic attractants, cylindrical traps made from sticky paper and containing synthetic attractants and McPhail traps containing synthetic attractants or torula yeast indicates that cylindrical traps made from sticky paper and containing ammonium acetate, putrescine and trimethyl amine is the most effective in the capture of *C. capitata* compared to other traps tested. Traps capture of *A. ludens* is also greatest in the cylindrical sticky paper traps containing ammonium acetate, putrescine and trimethyl amine compared to other traps.

The novel combination of traps, especially sticky paper traps, and the chemical stimuli including the synergist of the invention provides a tool for fruit fly detection and population density estimation as well as a means for control of these pests. The ability of the invention to attract both sexes of Mediterranean fruit flies suggests the following beneficial economic applications: (1) the detection of a new infestation; and (2) the monitoring of existing adult populations in order to predict future infestation levels to better schedule (and reduce) treatment with conventional pesticides.

A particular advantage of the invention is that it includes chemicals that are food-based attractants with a synergist and that it attracts both female and male Mediterranean fruit flies and Mexican fruit flies.

Another advantage of the invention is that it allows detection of populations and changes in populations of Mediterranean and Mexican fruit flies, and provides a means to control these fruit flies in fruit crops to reduce or prevent losses caused by the pests.

Trap Construction

Figure 5:
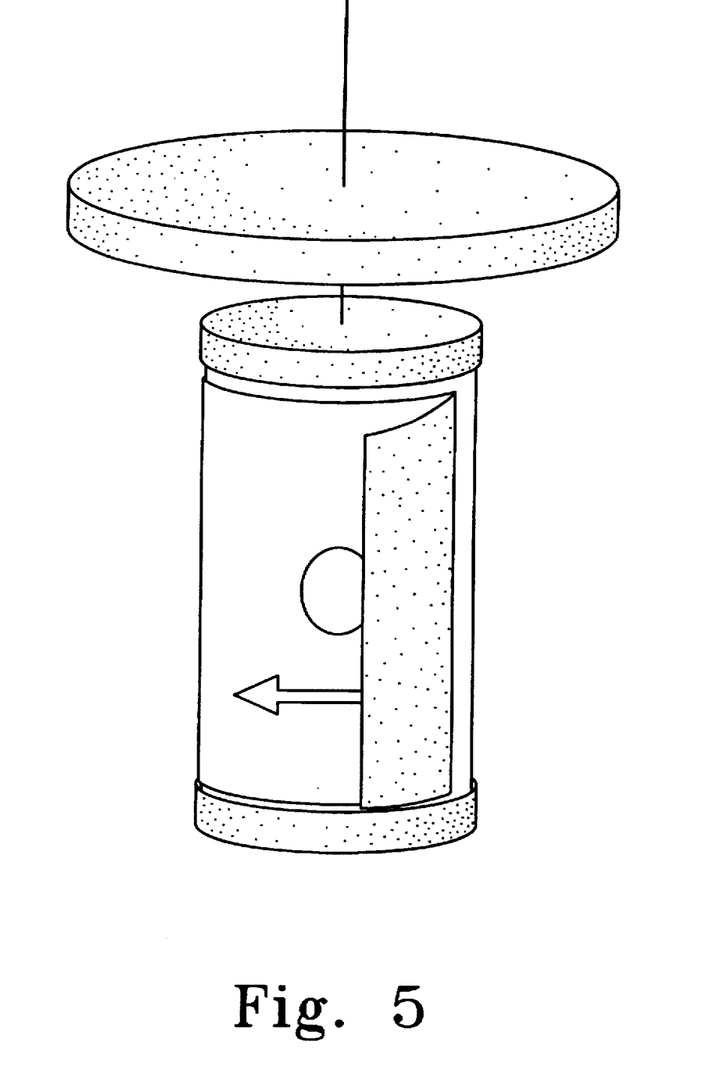
FIG. 5 is a drawing of a sticky-paper cylindrical trap made with dark green fruit fly adhesive paper.

Cylinderical traps are prepared from commercially produced fruit fly adhesive paper and were prepared as described previously in Heath et al (*Fla. Entomol.*, Volume 79, 37–48, 1996; herein incorporated by reference) (FIG. 5). Any adhesive paper is useful. Cylindrical traps are made most preferably from green adhesive paper supplied by the Atlantic Paste and Glue Co.,Inc.(Brooklyn, N.Y.). Briefly, the traps are prepared by rolling a 15.0 cm wide×30.0 cm long rectangular piece of the adhesive paper containing three 2.2 cm diameter holes cut out along the lengthwise center line spaced 10 cm apart left and right of center. The adhesive paper is made into a cylinder using a 9.0 cm diameter cylinder as a form and glued together using the adhesive supplied with the paper. A rain guard is used with this trap to protect the paper trap body and is made from the top half of a 150×15 mm petri dish (P/N#3488–b28, Thomas Scientific, Swedesboro, N.J.). Any material that will provide protection from rain is useful as a rain guard. A 5 cm piece of 9.0 cm OD diameter cylinder cut from polyvinyl chloride tubing (Hughs supply, Gainesville, Fla.) is glued to the center underside of the petri dish, which provides a holder for the trap body. The petri dish is drilled with a 0.16 cm hole through the center and a 35 cm long piece of 20 gauge galvanized steel wire is threaded through the hole and the wire is bent into a hook for hanging in a tree. The protective paper supplied with the adhesive paper is removed when the traps are placed in the field to expose the sticky trap surface. Trap bodies are replaced only when the number of flies preclude the continued use of the trap.

Figure 6:
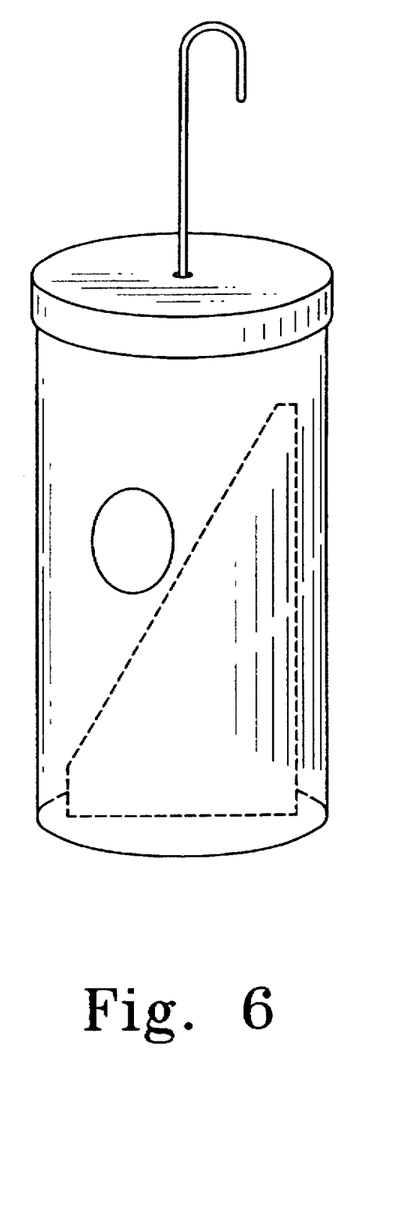
FIG. 6 is a drawing of a open bottom opaque cylindrical trap.

The open bottom opaque traps (Heath et al, *Fla. Entomol.*, Volume 79, 144–153, 1996; herein incorporated by reference) were constructed similar to that of the adhesive paper traps. The main body of the opaque cylindrical trap, however, was constructed from a 15.0 cm wide×30.0 cm long rectangular piece of 0.025 cm thick opaque green plastic (Faulkner Plastics, Gainesville, Fla.). A top cap was made using standard 100×15 mm laboratory grade plastic petri dishes IP/N #3488-B28, Thomas Scientific, Swedesboro, N.J.). The petri dish was glued shut using methylene chloride. The petri dish bottom is smaller and fits inside the dish top forming a small groove into which the wall of the plastic cylinder (main body trap) fits. A 0.16 cm hole was drilled through the center of each glued petri dish. The top cap was oriented with the bottom of the petri dish facing the interior of the cylinder. The opaque cylinder was attached by heat sealing the plastic cylinder to the top cap. Additionally, a ring made from a 1.0 cm wide×9 cm diameter PVC pipe was heat sealed to the inside of the bottom of the plastic cylinder to maintain the cylinderical shape of the trap body. A 35 cm piece of 20 gauge galvanized steel wire was threaded through the top end cap and bent at a 450° angle to form a hook for placement of a sticky insert. Sticky inserts were made from two pieces of fluorescent yellow adhesive paper that were cut into 8×13 cm rectangles. The adhesive papers were glued together back to back, sticky surfaces out. A 5 mm hole was punched approximately 1.5 cm from the top edge through the center to provide a mechanism to hang the insert on the wire hook located in the trap body.

One of ordinary skill in the art could modify and substitute any material suitable for protecting, supporting and hanging the above described cylindrical traps.

Lures are taped to the inside of the PVC tubing and the synthetic food-based attractants are not replaced during the six weeks of trials. However, lures (described below) can be placed anywhere inside the trap body. In addition to adhesive paper traps containing synthetic lures, liquid protein-baited McPhail traps, which are bell-shaped glass traps with a water reservoir (Newell, supra) and open bottom cylindrical traps were tested. McPhail traps are baited with five torula yeast-borax pellets (ERA, Int.,Freeport, N.Y.) in 300 ml of water (Gilbert et al, Insect Trapping Guide. Pest Detection/Emergency Projects, State of California Department of Food and Agriculture, Sacramento, CALIF., 1984).

Synthetic Bait Food Based Attractant

The synthetic bait food based attractant includes a two component blend consisting of ammonium acetate and putrescine (AA+P) alone and in combination with either methyl amine (AA+P+MA), dimethyl amine (AA+P+DMA) or trimethyl amine (AA+P+TMA). The amines were obtained from Aldrich Chemical (St. Louis, Mo.) and used without purification. A commercial formulation of ammonium acetate, BioLure@ (Consep Inc., Bend, Oreg.), is used for all studies. The release rate from the ammonium acetate lure is approximately 300 μg/hr of ammonia which is equivalent to a medium release rate previously used (Heath et al, *J. Econ. Entomol.*, Volume 88, 1307–1315, 1995; U.S. patent application Ser. Nos. 08/647,211 filed May 09, 1996 which is a file wrapper continuation of patent application Ser. No. 08/231,213, filed Apr. 22, 1994, now abandoned; and 08/440,023, a divisional of 08/231,213, filed May 12, 1995; all herein incorporated by reference). An effective amount is defined as that quantity of chemical blend that provides a release rate of the blend from a membrane that attracts fruit flies to the location of a bait at a rate significantly higher than flies are attracted to a nonbaited location. Ammonium acetate is contained in a release membrane made from, for example, polyethylene, polypropylene, polyvinylchloride, mylar, and acrylic as described in Leonhardt et al, Insect Pheromone Technology: Chemistry and Applications, ACS Symposium Series 190, 1982 and Kydonisus, Controlled Release Pesticides, ACS Symposium Series 53, 1977; which are herein incorporated by reference. A commercially available preparation of ammonium acetate from a release membrane called BioLure® (Concep Inc., Bend, Oreg.) can also be used. Additionally, the amount of ammonia and acetic acid can be quantified as described in Example 1 below. A preferred release rate range for ammonia is approximately about 40 μg/hour to 600 μg/hour. A more preferred range of release rate is 45–400 μg/hour. A most preferred amount is 45, 120, and 400 μg/hour for the low, medium, and high dose respectively. A preferred release rate range for acetic acid is approximately about 1.0 μg/hour to 16 μg/hour. A more preferred range of release is 1.5 to 13

µg/hour. A most preferred amount is 1.5, 3, and 13 µg/hour for low, medium, and high dose respectively. Putrescine (1,4-diaminobutane) lures are prepared using a polyethylene membrane system previously described (Epsky et al, *Environ. Entolmol.*, Volume 24, 1387–1395, 1995 herein incorporated by reference). It can also be placed in a vial as a substantially pure liquid preparation. A preferred range for 1,4 diaminobutane is approximately about 25–300 µl of a substantially pure liquid preparation (neat) of 1,4 diaminobutane. A more preferred range is approximately about 50–200 µl of a substantially pure liquid preparation 1,4 diaminobutane as described above. A most preferred amount is 50, 100, and 200 µl for a low, medium and high dose respectively. Research shows that ammonia and putrescine are released by protein baits and that when ammonium acetate and putrescine are used in combination without interference from other chemicals released by protein baits, they are highly attractive to fruit flies.

The substituted methyl amine lures are formulated using the same membrane system as used for the ammonium acetate lure (Biolure@, Consep, Inc., Bend, Oreg.) and test formulations contain 5 grams of the hydrochloride salt.

Factors such as insect population density, age-structure of the target population, temperature, wind velocity, and release rate will influence the response of the flies and thus the actual number of flies trapped. Factors such as temperature, wind velocity and release substrate will influence chemical release rate. The amount of compound in a particular set of circumstances that will provide a release rate within the effective range can readily be determined by a dose response field test as previously described in the United States Patent Applications cited supra.

USES OF THE INVENTION

The invention is used as a monitoring, control, and/or detection tool. One method is to deploy the trap and tabulate the catch to determine size and location of fruit fly infestation. Economic use of appropriate pest management systems can then be determined. The method of trapping the flies can also serve as a control method.

The invention is useful in combination with insecticide application or other control measures. The invention is used to attract flies to the trap where they become stuck and die.

Another method is for control of fruit flies by using the invention to detect the location and boundaries of localized fruit fly infestations and employ in the area chemosterilants, bioregulator agents, parasites, predators or other biological control agents for fruit flies.

EXAMPLES

The following examples illustrate the use of the invention for the control of frugivorous pest insects. Data converted to percentage per trap per sample date for statistical analysis were assessed by the BOX-COX procedure (Box et al, Statistics for Experimenter. An Introduction to Design, Data Analysis and Model Building, J. Wiley and Sons, New York, N.Y. 1978) and were transformed when necessary to stabilize the variance prior to analysis. Data were analyzed by one-way analysis of variance using Proc GLM (SAS Institute, SAS/STAT guide for personal computers version 6 edition. SAS Institute, Cary, N.C.) followed by least significant difference test (LSD, P=0.05) for mean separation. Field trials were conducted in Finca Santa Maria Xalapan in a mixed planting of coffee and citrus, located near Palin, Guatemala. The examples are intended to further illustrate the invention and are not intended to limit the scope of the invention as defined by the claims.

Example 1

The first field trials compare sticky paper cylinderical traps baited with ammonium acetate and putrescine (AA+P), ammonium acetate, putrescine and methylamine (AA+P+MA), ammonium acetate, putrescine and dimethylamine (AA+P+DA), ammonium acetate, putrescine and trimethylamine (AA+P+TA), and McPhail traps containing torula. These trials were run as no-choice tests, therefore there was one trap per citrus tree and all five traps were placed approximately 10 m apart along a line. Treatment placement within a line was random and there were five lines of traps with two lines of trees without traps between each baited line. Traps were checked every two to three days, and numbers of female and male *C. capitata* and *A. ludens* were recorded. Traps were moved sequentially at time of sampling. Adhesive paper trap bodies were replaced as required and the McPhail traps were baited with fresh torula yeast solution every other week. The torula yeast solution was recycled the other sample times. Water was added to bring the liquid level back to 300 ml if needed. Synthetic lures were not replaced throughout the study. Tests were conducted for a six week period for a total of 16 consecutive replicates.

Figure 1A:
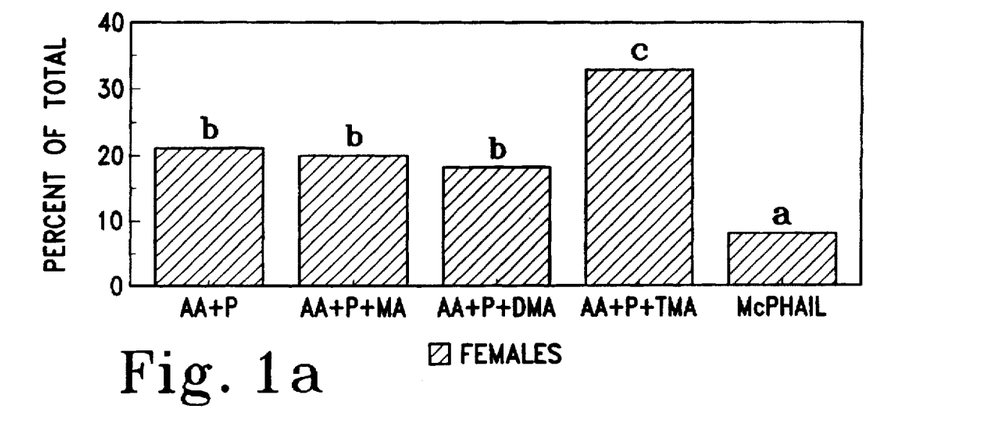
FIG. 1a is a graph showing percentage of *Ceratitis capitata* females captured in sticky cylinderical traps baited with ammonium acetate and putrescine (AA+P), ammonium acetate, putrescine and methylamine (AA+P+MA), ammonium acetate, putrescine and dimethylamine (AA+P+DA), ammonium acetate, putrescine and trimethylamine (AA+P+TMA), and McPhail traps containing torula. Bars headed by the same letter within a graph are not significantly different (LSD mean separation test on square root $|x|$ transformed (females and total) or non-transformed data (males), $P=0.05$; non-transformed means presented.
Figure 1B:
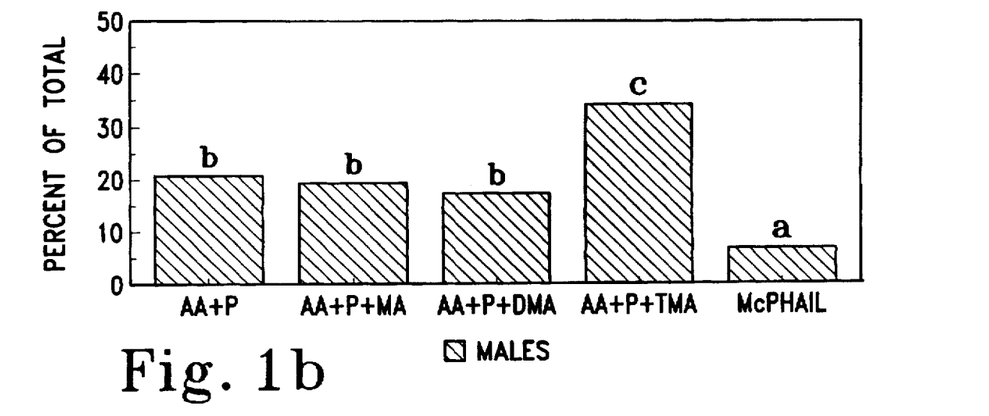
FIG. 1b is a graph showing percentage of *Ceratitis capitata* males captured in sticky cylinderical traps baited with ammonium acetate and putrescine (AA+P), ammonium acetate, putrescine and methylamine (AA+P+MA), ammonium acetate, putrescine and dimethylamine (AA+P+DMA), ammonium acetate, putrescine and trimethylamine (AA+P+TMA), and McPhail traps containing torula. Bars headed by the same letter within a graph are not significantly different (LSD mean separation test on square root $|x|$ transformed (females and total) or non-transformed data (males), $P=0.05$; non-transformed means presented.
Figure 1C:
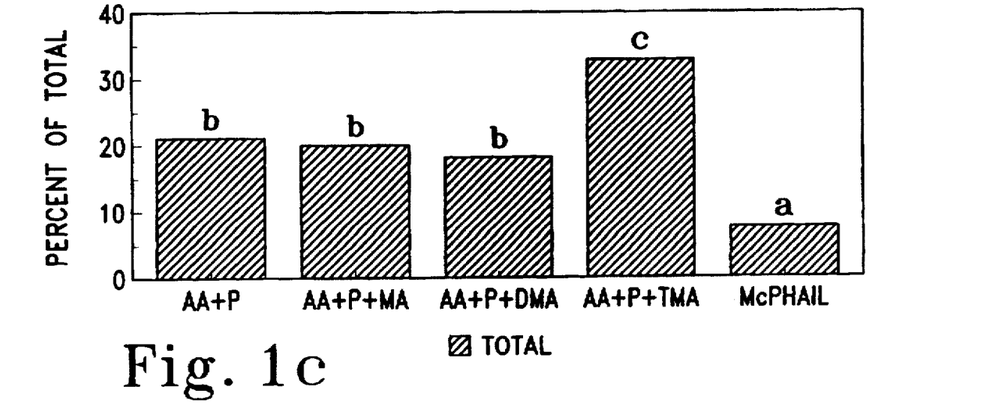
FIG. 1c is a graph showing percentage of *Ceratitis capitata* females plus males captured in sticky cylinderical traps baited with ammonium acetate and putrescine (AA+P), ammonium acetate, putrescine and methylamine (AA+P+MA), ammonium acetate, putrescine and dimethylamine (AA+P+DA), ammonium acetate, putrescine and trimethylamine (AA+P+TMA), and McPhail traps containing torula. Bars headed by the same letter within a graph are not significantly different (LSD mean separation test on square root $[x]$ transformed (females and total) or non-transformed (males), $P=0.05$; non-transformed means presented.
Figure 2A:
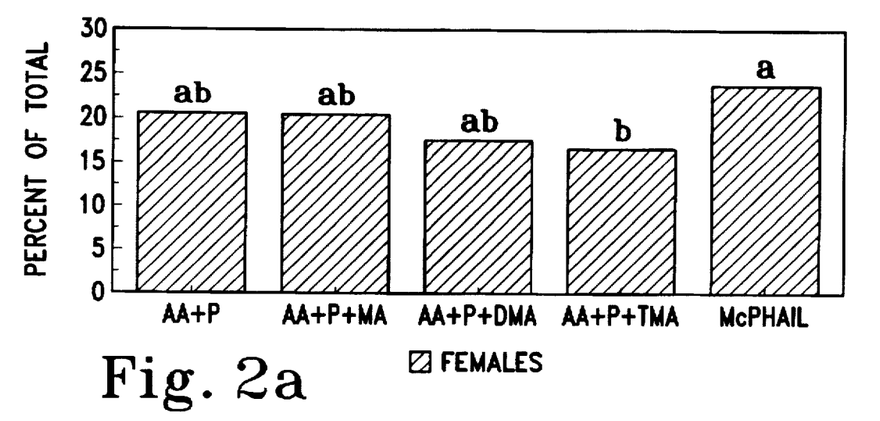
FIG. 2a is a graph showing percentage of *Anastrepha ludens* females captured in sticky cylinderical traps baited with ammonium acetate and putrescine (AA+P), ammonium acetate, putrescine and methylamine (AA+P+MA), ammonium acetate, putrescine and dimethyl amine (AA+P+DMA), ammonium acetate, putrescine and trimethyl amine (AA+P+TMA), and McPhail traps containing torula yeast (McPhail). Bars headed by the same letter within a graph are not significantly different (LSD mean separation test on log[x] transformed data, $P=0.05$; nontransformed means presented).
Figure 2B:
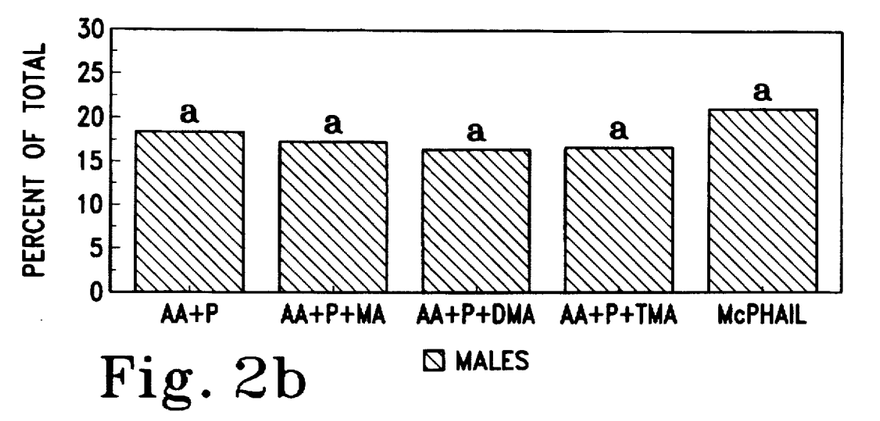
FIG. 2b is a graph showing percentage of *Anastrepha ludens* males captured in sticky cylinderical traps baited with ammonium acetate and putrescine (AA+P), ammonium acetate, putrescine and methylamine (AA+P+MA), ammonium acetate, putrescine and dimethyl amine (AA+P+DMA), ammonium acetate, putrescine and trimethyl amine (AA+P+TMA), and McPhail traps containing torula yeast (McPhail). Bars headed by the same letter within a graph are not significantly different (LSD mean separation test on log $|x|$ transformed data, $P=0.05$; nontransformed means presented).
Figure 2C:
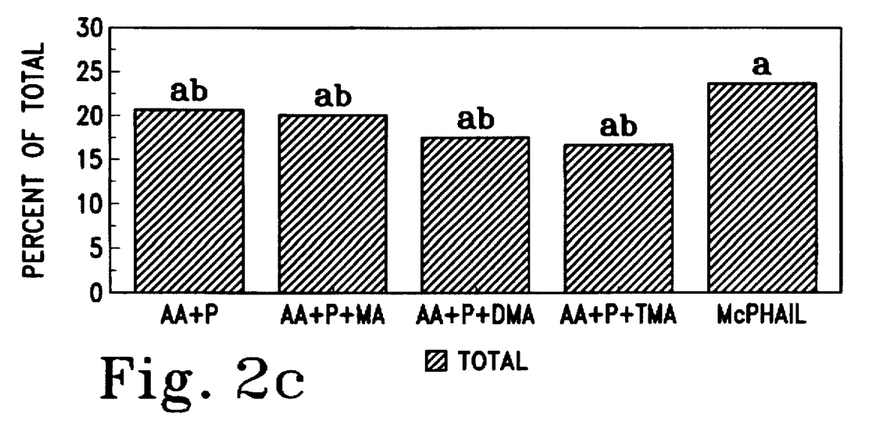
FIG. 2c is a graph showing percentage of *Anastrepha ludens* females plus males captured in sticky cylinderical traps baited with ammonium acetate and putrescine (AA+P), ammonium acetate, putrescine and methylamine (AA+P+MA), ammonium acetate, putrescine and dimethyl amine (AA+P+DMA), ammonium acetate, putrescine and trimethyl amine (AA+P+TMA), and McPhail traps containing torula yeast (McPhail). Bars headed by the same letter within a graph are not significantly different (LSD mean separation test on log[x] transformed data, $P=0.05$; nontransformed means presented).

Type of lure significantly affected capture of female ($F=38.65$; $df=4.54$; $P=0.0001$), male ($F=25.64$; $df=4.54$; $P=0.0001$), and total ($F=45.23$; $df=4.54$; $P=0001$) *C. capitata*. The capture was greatest in the traps baited with AA+P+TMA, intermediate in traps baited with AA+P or AA+P+MA or AA+P+DMA, and lowest in liquid protein-baited McPhail traps (FIG. 1). The results of the comparisons for capture of *A. ludens* among all five treatments are shown in FIG. 2. Liquid protein-baited McPhail traps captured the highest percentage of female and total *A. ludens* ([$F=3.68$; $df=4.54$; $P=0.0106$] and [$F=2.59$; $df=4.54$; $P=0.0475$], respectively). Capture in the traps baited with AA+P alone or in combination with methylamine or dimethyl amine was intermediate, and capture in traps baited with AA+P in combination with trimethyl amine was the lowest. There were no differences among any of the treatments for capture of male *A. ludens* ($F=0.67$; $df=4.54$; $P=0.6143$).

Interestingly, there is no difference in the percentage of *A. ludens* captured with synthetic lures tested. More female *A. ludens* were captured with the torula baited McPhail traps then the two component lure plus trimethyl amine. Previous reports (Robacker et al, 1993, supra; Robacker 1995, supra) indicated that a mixture of ammonium carbonate, putrescine and methyl amine was as attractive as torula yeast to laboratory reared *A. ludens* and irradiated *A. ludens*. In a subsequent publication (Robacker et al, *J. Chem. Ecol.*, Volume 22, 499–511, 1996) it was indicated that the use of ammonium acetate resulted in increase attraction of laboratory reared *A. ludens* compared to ammonium carbonate. In the current example, there is no increased attraction of wild *A. ludens* to ammonium acetate and putrescine lures containing methyl substituted ammonia.

Example 2

The second field trial compared the two component lure, ammonium acetate and putrescine (AA+P) and the two component lure plus trimethyl amine (AA+P+TMA) in both open bottom opaque plastic cylindrical traps (see below) and McPhail traps. Adhesive paper traps baited with the AA+P+TMA and McPhail traps baited with torula yeast solution were included in this study for comparative purposes. Synthetic lures were attached to the top of the McPhail traps and water containing a small amount of soap was added to the base of the McPhail to retain attracted flies.

The experiment was set up as 6 lines with all 6 trap-bait combinations within a line. Traps were placed individually in orange trees that were approximately 10m apart along a line. Treatment placement within a line was random, and there were two lines of trees without traps between each baited line. Traps were checked every 2–3 days and numbers of female and male *C. capitata* and *A. ludens* were recorded. The sticky inserts and adhesive paper trap bodies were replaced as required and traps were moved sequentially at time of sampling. The McPhail traps were baited with fresh torula yeast solution every other week, and the bait solution recycled the other sample times. Water was added to bring the liquid level back to 300 ml if needed and the synthetic lures were used throughout the study. Tests were conducted for a four week period for a total of 11 consecutive replicates.

Figure 3A:
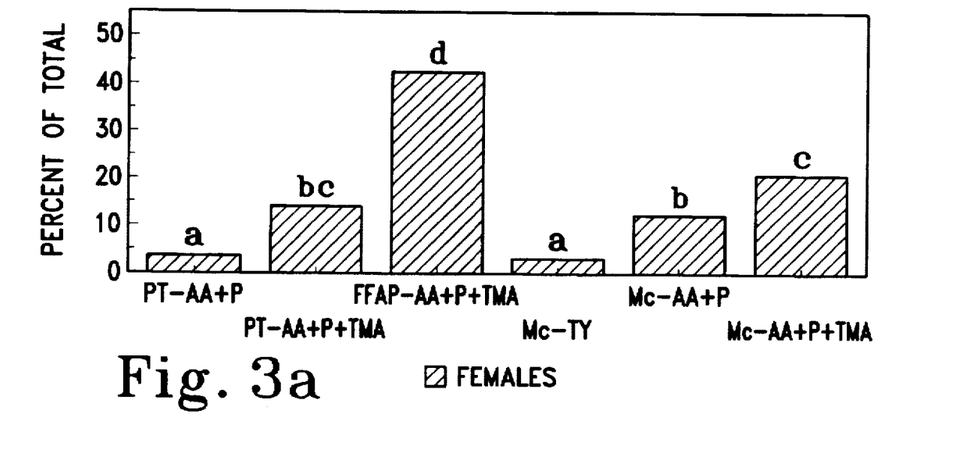
FIG. 3a is a graph showing percentage of *Ceratitis capitata* females captured in opaque open bottom cylinderical traps baited with ammonium acetate and putrescine (PT-AA+P), opaque open bottom cylinderical traps with ammonium acetate, putrescine and trimethylamine (PT-AA+P+TMA), sticky cylinderical traps baited with ammonium acetate, putrescine and trimethyl amine (FFAP-AA+P+TMA), McPhail traps baited with torula yeast (Mc-Ty), McPhail traps baited with ammonium acetate and putrescine (Mc-AA+P), McPhail traps baited with ammonium acetate, putrescine and trimethyl amine (Mc-AA+P+TMA). Bars headed by the same letter within a graph are not significantly different (LSD mean separation test on square root $|x+0.5|$ transformed data, $P=0.05$; non-transformed means presented).
Figure 3B:
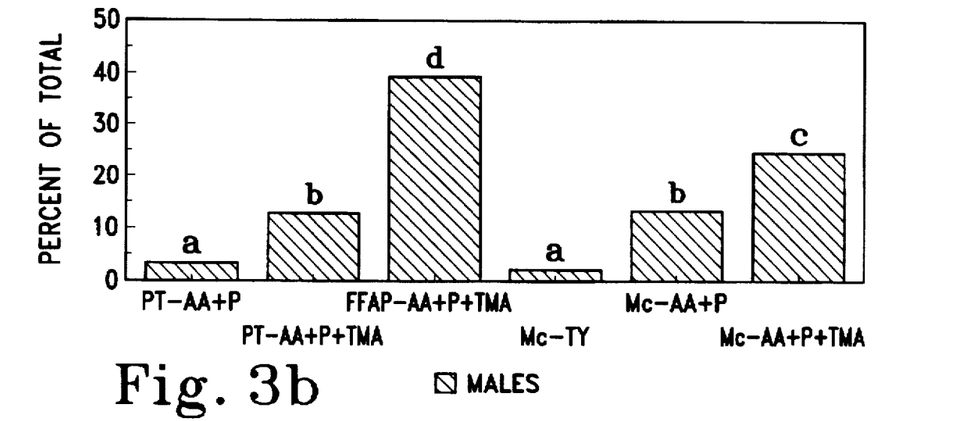
FIG. 3b is a graph showing percentage of *Ceratitis capitata* males captured in opaque open bottom cylinderical traps baited with ammonium acetate and putrescine (PT-AA+P), opaque open bottom cylinderical traps with ammonium acetate, putrescine and trimethylamine (PT-AA+P+TMA), sticky cylinderical traps baited with ammonium acetate, putrescine and trimethyl amine (FFAP-AA+P+TMA), McPhail traps baited with torula yeast (Mc-Ty), McPhail traps baited with ammonium acetate and putrescine (Mc-AA+P), McPhail traps baited with ammonium acetate, putrescine and trimethyl amine (Mc-AA+P+TMA). Bars headed by the same letter within a graph are not significantly different (LSD mean separation test on square root $|x+0.5|$ transformed data, $P=0.05$; non-transformed means presented).
Figure 3C:
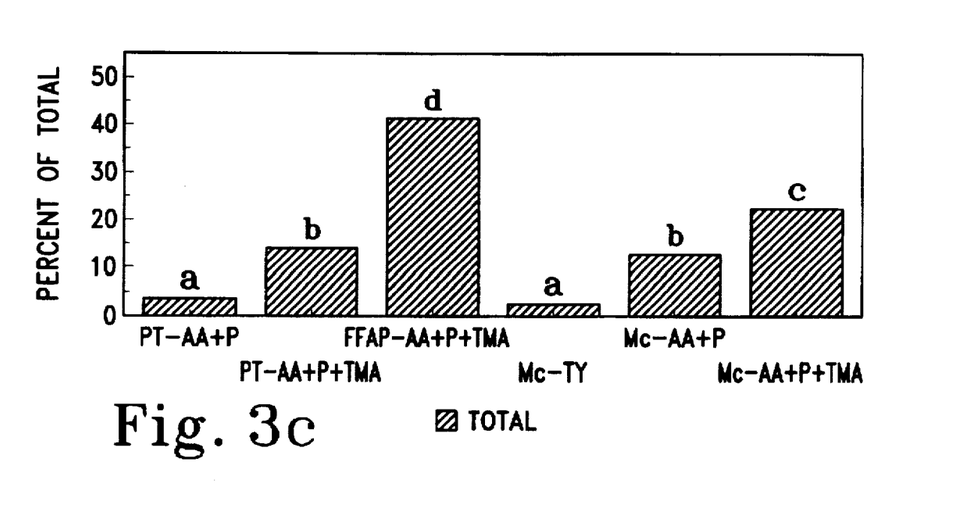
FIG. 3c is a graph showing percentage of *Ceratitis capitata* females plus males captured in opaque open bottom cylinderical traps baited with ammonium acetate and putrescine (PT-AA+P), opaque open bottom cylinderical traps with ammonium acetate, putrescine and trimethylamine (PT-AA+P+TMA), sticky cylinderical traps baited with ammonium acetate, putrescine and trimethyl amine (FFAP-AA+P+TMA), McPhail traps baited with torula yeast (Mc-Ty), McPhail traps baited with ammonium acetate and putrescine (Mc-AA+P), McPhail traps baited with ammonium acetate, putrescine and trimethyl amine (Mc-AA+P+TMA). Bars headed by the same letter within a graph are not significantly different (LSD mean separation test on square root [x+0.5] transformed data, P=0.05; non-transformed means presented).
Figure 4A:
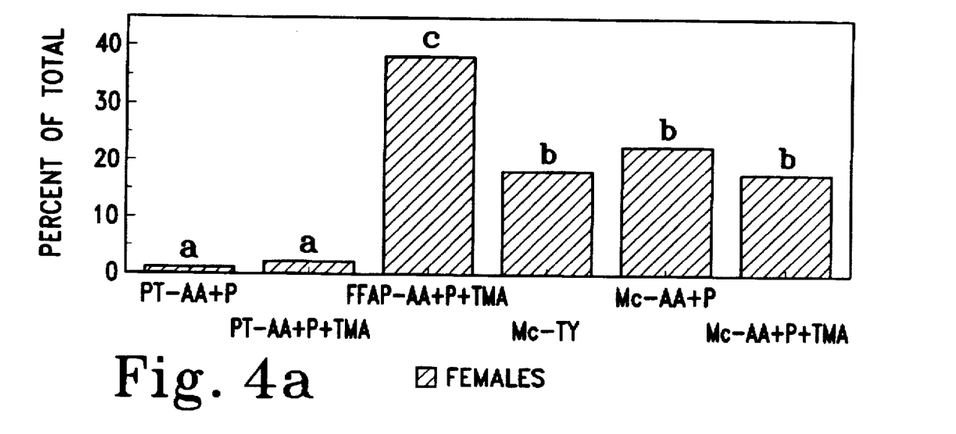
Figure 4B:
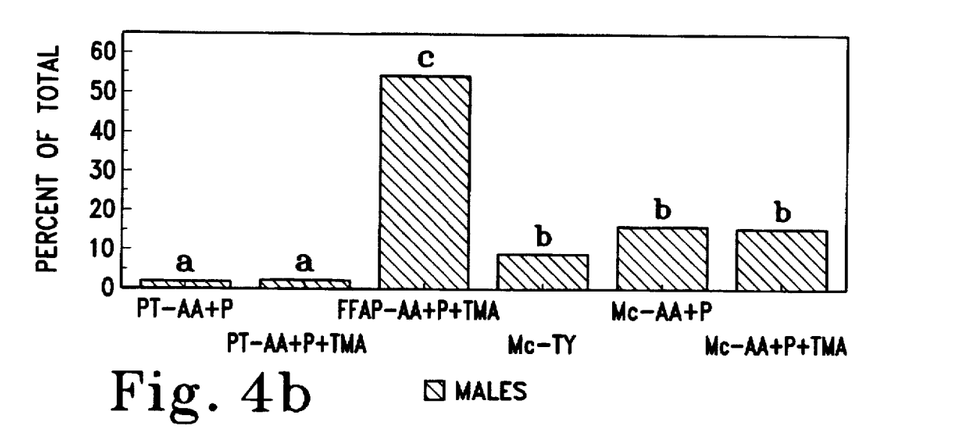
Figure 4C:
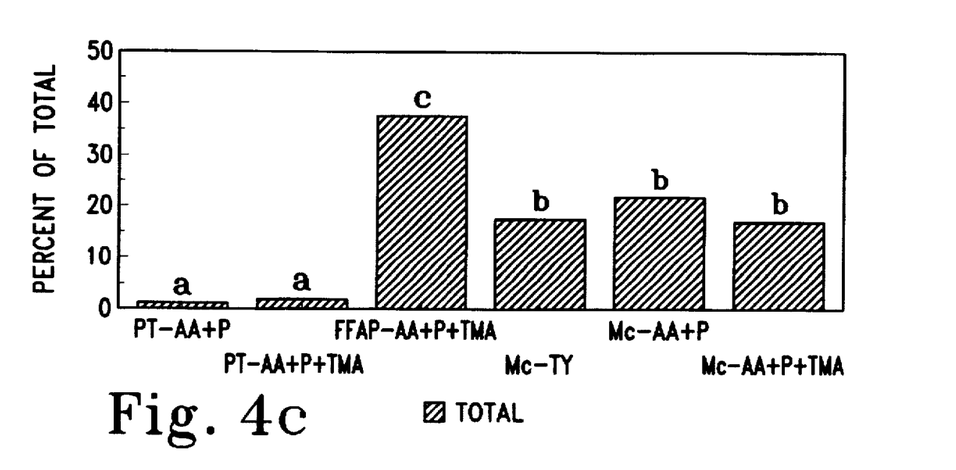

Trap and lure combination affected capture of female (F=59.56; df=5,60; P=0.0001), male (F=50.16; df=5,60; P=0.0001) and total (F=75.13; df=5,60; P=0.0001) *C. capitata* (FIG. 3). The most effective trap was the adhesive paper trap baited with AA+P+TMA, the next most effective traps were the McPhail trap and the opaque open bottom dry trap baited also baited with AA+P+TMA. The capture in liquid protein-baited McPhail traps and in the opaque open bottom dry trap baited AA+P was AA+P was the lowest. Capture in McPhail traps baited with AA+P equaled the capture in opaque open bottom dry traps baited with AA+P+TMA but was less than the capture in McPhail traps baited with the combination of AA+P+TMA. Trap and lure combination also affected capture of female (F=60.05; df=5,60; P=0.0001), male (F+79.22; df=5,60; P=0.001) and totals (F=77.03; df=5,60; P=0.0001) *A.ludens* (FIG. 4). The McPhail traps, regardless of bait used, captured intermediate percentages of *A.ludens* and the lowest capture was in opaque open bottom dry plastic traps.

While the adhesive paper trap baited with the three component synthetic lure was the most effective in capturing *C. capitata*, the performance of this lure improved trap capture when used in either a McPhail trap or an opaque open bottom plastic trap compared to the two component lure. In this study, the three component lure used in either an adhesive paper trap, McPhail trap and a McPhail trap baited with the two component lure was more effective then either McPhail trap with torula yeast or opaque open bottom plastic traps with the two component lure. In these studies, adhesive paper traps baited with the three component lure was the most effective trap for capture of *A.ludens*. No differences in percentage of *A. ludens* captured were observed for McPhail traps baited with either torula yeast, the two component or three component synthetic lures. The performance of the opaque open bottom traps for capture of *A. ludens* was significantly less then other traps tested and indicate that this trap design may severally compromise the capture of *A. ludens*.

Example 3

Field trials were conducted to determine if trimethyl amine is an attractant or functions as a synergist with ammonium acetate and putrescine. Traps and lures tested included 1) an unbaited sticky paper cylindrical trap (blank), 2) a sticky trap baited with trimethyl amine alone; 3) a sticky trap baited with ammonium acetate, putrescine and trimethyl amine, and 4) a McPhail trap baited with torula yeast solution, as described in the examples above. All treatments were placed randomly within a line, and there were five lines of traps. Fly capture was monitored over a two week period. Fly counts were made every two to three days for a total of four consecutive replicates. Capture of Mediterranean fruit flies was very low and precluded statistical analysis. However, of the 55 male Mediterranean fruit flies captured, 53 were captured in ammonium acetate plus putrescine plus trimethyl amine-baited trap, 1 in the blank trap, and 1 in the McPhail trap. During this test 82 female Mediterranean fruit flies were captured. Eighty of the females were captured in the trap containing ammonium acetate plus putrescine and trimethyl amine, and the other two females were captured in the torula yeast baited McPhail trap. A total of 166 male Mexican fruit flies were captured during this trial. Of these 77 were captured in the traps containing ammonium acetate plus putrescine plus trimethyl amine, 34 in blank traps, 46 in McPhail traps and 9 in the traps baited with trimethyl amine. A total of 135 female Mexican fruit flies were captured. 59 were captured in the ammonium acetate plus putrescine plus trimethyl amine, 8 in blank traps, 60 in McPhail traps and 8 in traps baited with trimethyl amine.

The forgoing description is for the purpose of illustration. Others skilled in the art can apply the knowledge described to other frugivorous pest insects. Such detail is solely for that purpose and those skilled in the art can make variations therein without departing from the spirit and scope of the invention.

We claim:

1. A method for selectively monitoring and/or controlling frugivorous pest insects comprising placing a trapping system comprising a trapping means containing an effective amount of a frugivorous pest insect attractant composition consisting essentially of ammonium acetate in a release membrane and putrescine, and a synergist for said attractant composition in an area where frugivorous pests are to be attracted.

2. The method of claim 1 wherein said synergist is trimethyl amine.

3. A trapping system for monitoring and/or controlling frugivorous pest insects comprising a trapping means, an effective amount of a frugivorous pest insect attractant composition consisting essentially of ammonium acetate in a release membrane and putrescine for attracting said pest insects, and a synergist for said attractant composition.

4. The trapping system of claim 3 where said synergist is trimethyl amine.

* * * * *